US011475212B2

(12) United States Patent
Bellero et al.

(10) Patent No.: US 11,475,212 B2
(45) Date of Patent: Oct. 18, 2022

(54) SYSTEMS AND METHODS FOR GENERATING AND MODIFYING DOCUMENTS DESCRIBING SCIENTIFIC RESEARCH

(71) Applicant: Otsuka Pharmaceutical Development & Commercialization, Inc., Rockville, MD (US)

(72) Inventors: Michael Bellero, Toms River, NJ (US); William Hannon, Poolesville, MD (US); Boris Reznichenko, Staten Island, NY (US); Karen Rutkowski, Middlesex, NJ (US); Brian Geldziler, Somerset, NJ (US)

(73) Assignee: Otsuka Pharmaceutical Development & Commercialization, Inc., Rockville, MD (US)

( * ) Notice: Subject to any disclaimer, the term of this patent is extended or adjusted under 35 U.S.C. 154(b) by 0 days.

(21) Appl. No.: 17/374,802

(22) Filed: Jul. 13, 2021

(65) Prior Publication Data

US 2021/0342523 A1  Nov. 4, 2021

Related U.S. Application Data

(63) Continuation of application No. 15/946,691, filed on Apr. 5, 2018, now abandoned.

(60) Provisional application No. 62/482,526, filed on Apr. 6, 2017.

(51) Int. Cl.
*G06F 40/166* (2020.01)
*G16H 15/00* (2018.01)
*G06F 40/14* (2020.01)
*G06F 40/295* (2020.01)

(52) U.S. Cl.
CPC ............ *G06F 40/166* (2020.01); *G06F 40/14* (2020.01); *G06F 40/295* (2020.01); *G16H 15/00* (2018.01)

(58) Field of Classification Search
CPC ........ G06F 40/166; G06F 40/14; G06F 40/56; G06F 40/295; G16H 15/00; G16H 10/20
USPC ....................................................... 715/255
See application file for complete search history.

(56) References Cited

U.S. PATENT DOCUMENTS

| | | | | |
|---|---|---|---|---|
| 6,542,905 B1 * | 4/2003 | Fogel | ..................... | G06Q 10/06 |
| 7,818,665 B1 * | 10/2010 | Russin | .................. | G06F 40/143 |
| | | | | 715/239 |
| 7,983,935 B1 * | 7/2011 | Carricarte | .............. | G06Q 10/00 |
| | | | | 705/2 |

(Continued)

*Primary Examiner* — Andrew R Dyer
(74) *Attorney, Agent, or Firm* — Pillsbury Winthrop Shaw Pittman, LLP

(57) ABSTRACT

Systems and methods are disclosed for data driven document creation and modification. The systems and methods include obtaining a first dataset having data records associated with entities, obtaining a list of entities associated with a first subset of data records in the first dataset, and obtaining configuration information, wherein the configuration information includes rules for identifying logical relationships in the data records and wherein the configuration information is specified using a vector-oriented language. The systems and methods further include extracting, for each entity in the list of entities, based on the rules, data records from the first subset of data records associated with the entity and generating a document for each entity in the list of entities using the extracted data records and the configuration information.

17 Claims, 18 Drawing Sheets

(56) References Cited

U.S. PATENT DOCUMENTS

| | | | | |
|---|---|---|---|---|
| 8,560,968 B1* | 10/2013 | Nair | G16H 40/63 | 715/810 |
| 8,667,385 B1* | 3/2014 | Mui | G06F 16/904 | 715/205 |
| 8,850,321 B2* | 9/2014 | Seeger | G06F 11/3055 | 709/224 |
| 10,311,206 B2* | 6/2019 | Boloor | G16H 15/00 | |
| 10,319,476 B1* | 6/2019 | LaBorde | G06N 3/04 | |
| 10,811,125 B2* | 10/2020 | Bao | G16H 10/60 | |
| 2003/0229852 A1* | 12/2003 | Uramoto | G06F 40/143 | 715/237 |
| 2005/0050096 A1* | 3/2005 | Gomes | G06Q 10/06 | |
| 2005/0108639 A1* | 5/2005 | Fields | G06Q 10/107 | 715/255 |
| 2006/0155398 A1* | 7/2006 | Hoffberg | G06V 40/103 | 700/86 |
| 2006/0173716 A1* | 8/2006 | Wang | G16H 40/67 | 600/300 |
| 2007/0106754 A1* | 5/2007 | Moore | G16H 10/60 | 707/E17.116 |
| 2010/0036860 A1* | 2/2010 | Hiura | G06F 40/166 | 707/634 |
| 2010/0115394 A1* | 5/2010 | Oshima | G06F 40/143 | 715/234 |
| 2010/0179821 A1* | 7/2010 | Gedeon | G16H 20/10 | 705/2 |
| 2011/0087954 A1* | 4/2011 | Dickerman | G06F 40/18 | 715/219 |
| 2011/0145018 A1* | 6/2011 | Fotsch | G06Q 50/20 | 705/2 |
| 2011/0196861 A1* | 8/2011 | Egnor | G06F 16/958 | 707/723 |
| 2012/0089893 A1* | 4/2012 | Bousamra | A61B 5/4839 | 711/E12.001 |
| 2012/0209625 A1* | 8/2012 | Armstrong | G06Q 10/10 | 705/2 |
| 2012/0221347 A1* | 8/2012 | Reiner | G06Q 10/00 | 705/2 |
| 2013/0239036 A1* | 9/2013 | MacDonald | G06F 16/283 | 707/E17.014 |
| 2014/0033025 A1* | 1/2014 | Mukherjee | H04N 21/8133 | 715/246 |
| 2014/0088393 A1* | 3/2014 | Bernstein | G16H 50/20 | 600/365 |
| 2014/0285490 A1* | 9/2014 | Gilger | G16Z 99/00 | 345/440 |
| 2015/0213202 A1* | 7/2015 | Amarasingham | G16H 50/50 | 705/2 |
| 2015/0213206 A1* | 7/2015 | Amarasingham | G16H 50/30 | 705/2 |
| 2015/0213207 A1* | 7/2015 | Amarasingham | G16H 50/50 | 705/2 |
| 2015/0324075 A1* | 11/2015 | Schulze | G06F 40/134 | 715/760 |
| 2016/0004820 A1* | 1/2016 | Moore | H04W 4/21 | 705/3 |
| 2016/0048655 A1* | 2/2016 | Maitra | G16H 70/40 | 705/3 |
| 2016/0140320 A1* | 5/2016 | Moturu | G16H 20/70 | 434/236 |
| 2017/0235912 A1* | 8/2017 | Moturu | G16H 40/67 | 705/2 |
| 2017/0315978 A1* | 11/2017 | Boucher | G06F 40/14 | |
| 2017/0315979 A1* | 11/2017 | Boucher | G06F 40/197 | |
| 2017/0337329 A1* | 11/2017 | Liu | A61B 6/463 | |
| 2018/0025132 A1* | 1/2018 | Mabotuwana | A61B 5/7275 | 705/3 |
| 2018/0081859 A1* | 3/2018 | Snider | G06F 40/44 | |
| 2018/0189913 A1* | 7/2018 | Knopp | H04W 4/90 | |
| 2018/0358121 A1* | 12/2018 | Carolus | G06Q 10/06 | |
| 2019/0057191 A1* | 2/2019 | Bao | G16H 10/60 | |
| 2019/0272907 A1* | 9/2019 | Aldairy | G16H 70/40 | |
| 2019/0333644 A1* | 10/2019 | Lamarre | G16H 10/60 | |

\* cited by examiner

FIG. 3

Generate Narratives

Study Information | Referred/Auxiliary Information | AEs of Special Interest | Subject List
Clinically Significant Values | Treatment Phases | AE Terms Formatting | Generate

Abnormal Condition Lists

Test One ▼

Tests
- Aspartate Aminotransferase
- Albumin
- Alkaline Phosphatase
- Amorphous Crystals
- Amylase
- Aspartate Aminotransferase
- Barbiturates
- Basophils
- BASOPHILS, ABSOLUTE
- Benzodiazepine
- Benzoylecgonine
- Bicarbonate
- Bilirubin
- BLOOD
- Blood Urea Nitrogen
- Calcium
- Calcium Oxalate Crystals

Rules

Medical Test Name
- ECG Results
- Vital Signs

Aspartate Aminotransferase [DP] = [VAL] 29 [FOR SEX] F1

Conditions ▼ | Value [ ] | Sex Select... ▼

Sub-Conditions
○ AND  ○ OR  □ NOT  □ Include as Condition

Conditions ▼ | Visits 4 WEEK FOLLO ▼
Value [ ]

SYSTEMS AND METHODS FOR GENERATING AND MODIFYING DOCUMENTS DESCRIBING SCIENTIFIC RESEARCH

CROSS-REFERENCE TO RELATED APPLICATIONS

This application is a continuation of U.S. patent application Ser. No. 15/946,691, filed on Apr. 5, 2018, which claims benefit under 35 USC § 119(e) to U.S. Provisional Patent Application No. 62/482,526, filed on Apr. 6, 2017, the contents of each application is expressly incorporated herein by reference in their entireties.

BACKGROUND

Scientific research and study can result in the generation of many data sets over many intervals of time. Researchers must process the relevant data and generate descriptive narratives, documents, or reports about specific events and outcomes for individuals or subjects participating in the research or studies. These narratives, documents, or reports can also often include in-text tables and summary text or other specifically-formatted content that requires close attention when creating or updating. Additionally, regulations or other administrative policies can require that narratives be produced in particular formats and contain particular information. Because of the vast amount of data generated during a research study, preparing narratives for the various subjects can be an extremely tedious, time consuming, and error prone task. Moreover, as the source data is updated, the existing documents must be reprocessed to reflect the new information. Current manual systems and methods for reprocessing such documents typically involve a complete redo of the document generation. There exists a need to efficiently and effectively automate document generation, including narrative and report generation, in a manner that not only allows for accuracy in the creation of the documents, but that also provides an efficient way to quickly generate documents that satisfy the requirements associated with modern scientific research, which often include strict requirements on data storage, transformation, reproducibility, and presentation of information. Moreover, there exists a need to effectively and efficiently update those documents.

BRIEF DESCRIPTION OF THE DRAWINGS

Reference will now be made to the accompanying drawings showing example embodiments of this disclosure. In the drawings:

FIG. 3 is a diagram of an exemplary user interface, consistent with embodiments of the present disclosure.

FIG. 9 is a diagram of an exemplary user interface, consistent with embodiments of the present disclosure.

FIG. 12 is a diagram of an exemplary user interface, consistent with embodiments of the present disclosure.

FIG. 13 is an exemplary narrative, consistent with embodiments of the present disclosure.

FIG. 14 is an exemplary narrative, consistent with embodiments of the present disclosure.

DETAILED DESCRIPTION

Reference will now be made in detail to the exemplary embodiments implemented according to the present disclosure, the examples of which are illustrated in the accompanying drawings. Wherever possible, the same reference numbers will be used throughout the drawings to refer to the same or like parts.

Embodiments consistent with the present disclosure provide systems and methods for data driven document creation and modification. The disclosed technologies provide a mechanism to efficiently and accurately generate documents such as narratives or reports associated with scientific research. Systems and methods consistent with the present disclosure can automate the task of creating scientific narratives. Previous methods relied on tedious creation of individual narratives that resulted in error prone and time consuming results. Automated systems consistent with embodiments of the present disclosure allow for both consistency and accuracy in produced narratives by allowing for configuration of the individuals and types of information for which narratives are needed and using data driven analysis and processing to automatically generate those narratives. Moreover, the disclosed technologies provide systems and methods for using previously generated narratives that can contain researcher comments and annotations as a basis for generating a new narrative. The newly generated narratives can show differences between past narratives and retain manually created comments or annotations. Because systems and methods consistent with the present disclosure can update previously generated narratives, researchers can begin generating narratives before all of the data is collected or available. This provides a significant advantage in that researchers can begin the process of generating narratives much earlier in a research cycle. This can further allow researchers to identify potential problems or preliminary results much earlier. As new data is gathered, the disclosed systems and methods can incorporate that new data into updated narratives. The efficiency gains of the present disclosure can provide significant advantages over the previous techniques of document and narrative generation and greatly reduce the time needed to compile regulatory applications that can depend on those documents and narratives. Although the generation of narratives are described throughout the present disclosure, the use of this term is not intended to be limiting. Embodiments consistent with the present disclosure can be used to generate various types of output or reports based on an analysis of scientific data. The specific type of output can be dependent on the particular domain in which embodiments consistent with the present disclosure are being used.

Figure 1:
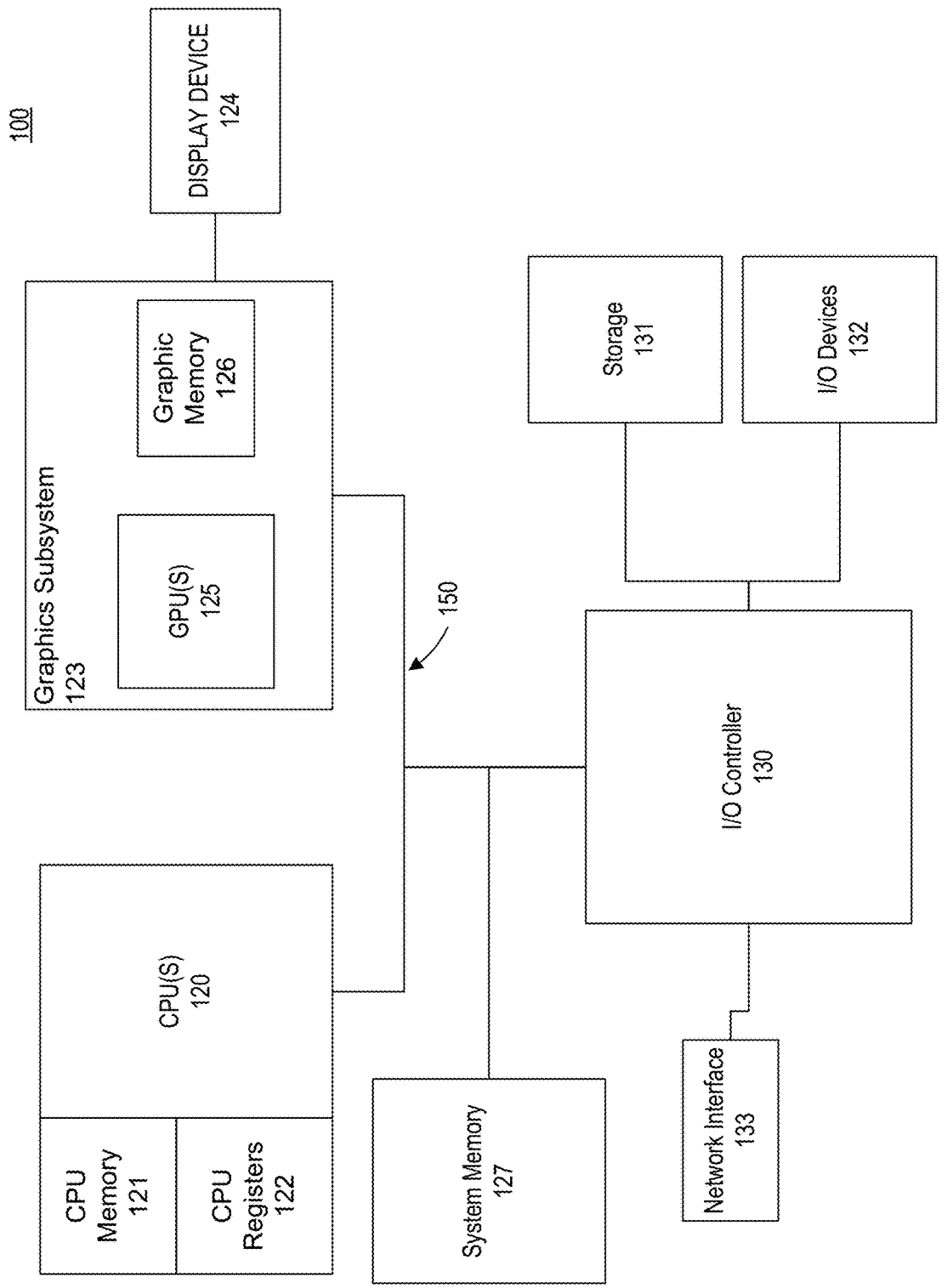
FIG. 1 is a block diagram of an exemplary computing device, consistent with embodiments of the present disclosure.

FIG. 1 is a block diagram of an exemplary computing device 100, consistent with embodiments of the present disclosure. Computing device 100 can include one or more central processing units (CPUs) 120, a graphics subsystem 123 with one or more GPUs 125 and graphic memory 126, a display device 124, system memory 127, I/O controller 130, storage 131, I/O devices 132, and network interface 133. The components of computing device 100 can be connected through a system bus 150. It is appreciated computing device 100 can use more or fewer components and organizations of components.

CPUs 120 can be any logic circuitry that responds to and processes instructions retrieved from the system memory 127, CPU cache 121, or CPU registers 122. CPUs 120 can be a single or multiple microprocessors, field-programmable gate arrays (FPGAs), or digital signal processors (DSPs) capable of executing particular sets of instructions stored in a memory (e.g., system memory 127), a cache (e.g., CPU cache 121), or registers (e.g., CPU registers 122). CPU registers 122 can store variable types of data. For example, these registers can store data, instructions, floating point values, conditional values, and/or addresses for locations in system memory 127. CPU registers 122 can include special purpose registers used to store data associated with the running process. The system memory 127 can include a tangible and/or non-transitory computer-readable medium, such as a flexible disk, a hard disk, a CD-ROM (compact disk read-only memory), MO (magneto-optical) drive, a DVD-ROM (digital versatile disk read-only memory), a DVD-RAM (digital versatile disk random-access memory), a flash drive and/or flash memory, processor cache, memory register, or a semiconductor memory. System memory 127 can be one or more memory chips capable of storing data and allowing any storage location to be directly accessed by CPUs 120. System memory 127 can be any type of random access memory (RAM), or any other available memory chip capable of operating as described herein. CPUs 120 can communicate with system memory 127 and other components via system bus 150. System bus 150 can bridge communication between components in computing device 100 including CPUs 120 and graphics subsystem 123. In some embodiments, CPUs 120, GPUs 125, system bus 150, or any combination thereof, can be integrated into a single processing unit. In some embodiments, additional components of computing device 100, such as I/O controller 130, network interface 133, storage 131, and I/O device 132, or any combination thereof, can further be integrated with CPUs 120 and graphics subsystem 123 in a single processing unit.

Graphics subsystem 123 can include one or more components for providing a graphics display (e.g., on display device 124). Graphics subsystem 123 can include GPUs 125. GPUs 125 can have a highly parallel structure making them more effective than general-purpose CPUs 120 for algorithms where processing of large blocks of graphical data can be performed in parallel. GPUs 125 can be any type of specialized circuitry that can manipulate and alter memory (e.g., graphic memory 126) to provide and/or accelerate the creation or manipulation of images for output to a display device (e.g., display device 124).

GPUs 125 can be capable of executing particular sets of instructions stored in system memory 127 or graphic memory 126 to manipulate graphical data stored in system memory 127 or graphic memory 126. For example, GPUs 125 can receive instructions transmitted by the CPUs 120 and processes the instructions in order to render graphics data stored in the graphic memory 126. Graphic memory 126 can be any memory space accessible by GPUs 125, including local memory, system memory, on-chip memories, and hard disk. GPUs 125 can enable displaying of graphical data stored in graphic memory 126 on display device 124.

Computing device 100 can also include input/output (I/O) controller 130. I/O controller 130 can provide an interface to input/output (I/O) devices 132 (e.g., a keyboard, mouse, or pointing device) connected through an I/O controller 130, which can communicate via system bus 150. I/O controller can communicate with various types of components through various types of connections (e.g., using, among others, serial and parallel port connections, SATA, IDE, PCI, USB, Thunderbolt, or Firewire).

I/O controller 130 can also communicate with a network interface 133. Network interface 133 can allow computing device 100 and the components of computing device 100 (e.g., CPUs 120) to connect to a network such as a LAN, WAN, MAN, or the Internet, through a variety of connections including, but not limited to, standard telephone lines, LAN or WAN links (e.g., 802.11, T1, T3, 56 kb, X.25), broadband connections (e.g., ISDN, Frame Relay, ATM), wireless connections, or some combination of any or all of the above. Network interface 133 can comprise a built-in network adapter, network interface card, PCMCIA network card, card bus network adapter, wireless network adapter, USB network adapter, modem or any other device suitable for interfacing computing device 100 to any type of network capable of communication and performing the operations described herein.

I/O controller 130 can also provide access to storage 131 which can be one or more mass storage devices such as a floppy disk drive for receiving floppy disks such as 3.5-inch, 5.25-inch disks or ZIP disks, a CD-ROM drive, a CD-R/RW drive, a DVD-ROM drive, a Blu-Ray drive, tape drives of various formats, a USB device, a hard-drive, a flash drive, redundant arrays of independent disks, or any other device suitable for storage.

Figure 2:
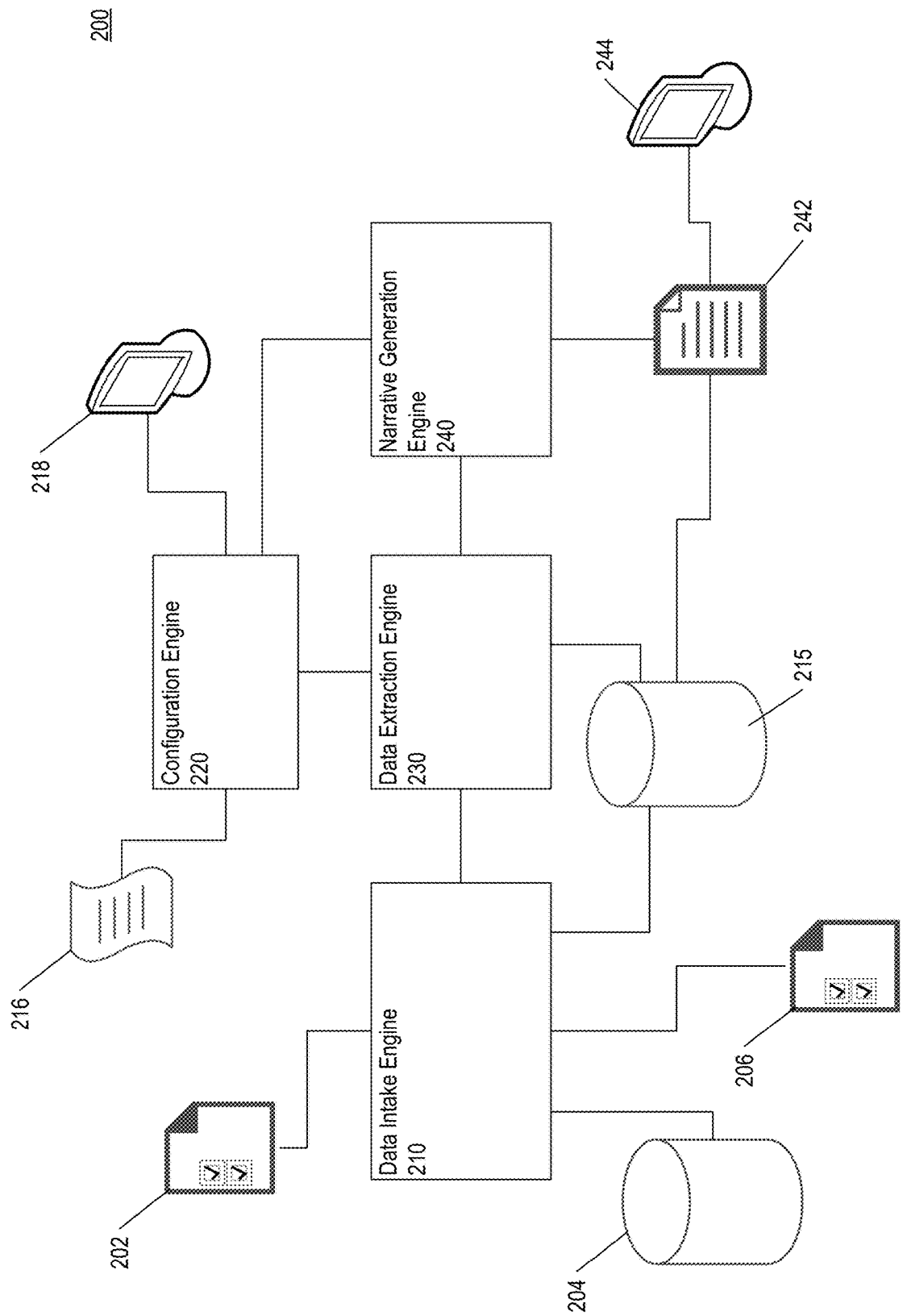
FIG. 2 is a block diagram of an exemplary system, consistent with embodiments of the present disclosure.

FIG. 2 is an exemplary system 200 for data driven document creation and modification consistent with embodiments of the present disclosure. In some embodiments, system 200 can be used to generate and update clinical narratives based on clinical and other data, including collected data or user specified data such as safety data. System 200 can include data intake engine 210, configuration engine 220, data extraction engine 230, and narrative generation engine 240. Data intake engine 210 can process data from data sources 202, 204, 206 and information or data stored in data storage 215. Data configuration engine 220 can receive input from and provide output to device 218. Device 218 can provide output from system 200 to a user and can receive input from a user using device 218. Moreover, configuration engine 220 can process data from configuration files 216 to configure system 200. Narrative generation engine can output narratives 242. Narratives 242 can be stored in data storage 215 and, in some embodiments, narratives and/or audit trail of the narrative generation can be displayed on device 244. System 200, data intake engine 210, data configuration engine 220, data extraction engine 230, and narrative generation engine 240 can be implemented using a computing device such as computing device 100 described in FIG. 1.

The components of system 200 can be implemented on a single computing device (e.g., computing device 100), each component of system 200 can be implemented on a separate computing device (e.g., a plurality of computing devices such as computing device 100), or some combination thereof, can utilize storage 131 and/or system memory 127 for storing data, and can utilize I/O devices 132 or network interface 133 for transmitting and/or receiving data. Moreover, each of device 218 and device 244 can be implemented using a separate computing device (e.g., computing device 100) or can be implemented on the same computing device (e.g., computing device 100) and can be used to provide output to a user and to receive input from a user. Each of data intake engine 210, configuration engine 220, data extraction engine 230, and narrative generation engine 240 can be a module, which is a packaged functional hardware unit designed for use with other components (e.g., portions of an integrated circuit) or a part of a program (stored on a computer readable medium) that performs a particular function or related functions. Each of these components is described in more detail below.

Data intake engine 210 is a module that can retrieve data from a variety of data sources. Each of these data sources can represent different types of data. For example, data source 202 and data source 206 can represent clinical data from clinical trials. Data source 202 can include data from an ongoing clinical study. Data source 206 can include data from past or related clinical studies. This data can be in various formats depending on the manner in which the data was produced or collected. Data intake engine can further utilize data stored in data source 204. Data source 204 can include, among other things, demographic or other information related to the individuals participating in a study. It is appreciated that the descriptions of data source 202, data source 206, and data source 204 as storing clinical and/or safety data associated with clinical trials is exemplary. In some embodiments for different domains and applications of system 200, data source 202, data source 206, and data source 204 may contain alternative types and formats of data.

Data intake engine 210 can retrieve data from the various data source. Because the data in different data sources can represent information occurring over different intervals of time and can have different data formats, data intake engine can process data from the data sources (e.g., data source 202, data source 206, and data source 204) and normalize the data into a consistent or common format. Data intake engine 210 can further append the raw or normalized data sets together in order to create a unified data set. The unified data set can be stored in, for example, data storage 215 and can be provided to data extraction engine 230 and the other components of system 200. In some embodiments, the unified data set can be provided to data extraction engine 230 and other components of system 200 without being permanently stored. The data sets shown in FIG. 2 are exemplary. It is appreciated that in some embodiments the number and type of data sets are unlimited.

Configuration Engine 220 is a module that can configure the format, content, and scope of narratives or documents generated by system 200 as well as configure automatic content updates to the narratives or documents. Configuration engine can utilize configuration scripts 216 or other configuration files to establish the configuration of system 200. Additionally, configuration engine 220 can receive direct input from a user via computing device 218.

Configuration engine 220 can utilize the provided configuration information to determine what information is used for the creation of a narrative. For example, Configuration engine 220 can specify the patients in a clinical study for which a narrative will be generated by system 200. Patients for inclusion in the narrative generation can be chosen directly or selected using a specified criteria provided to configuration engine 220. For example, configuration engine 220 can be instructed to include every patient sharing a certain demographic characteristic such as age or every patient experiencing a certain adverse event and adverse event category such as becoming pregnant, or testing positive for pregnancy, or every patient experiencing a certain response to the study. In this way, a user of system 200 can use configuration engine 220 to control the number and type of narratives generated by the system.

Configuration engine 220 can further be used to specify the logic and handling associated with certain adverse events. For example, during a clinical study, patients can experience a death serious adverse event, non-fatal serious adverse event, or an adverse event requiring a patient's discontinuation. Additional triggering of adverse events (e.g., adverse events of special interest) or positive pregnancy tests/pregnancy can also be utilized as part of the conditional logic within engine 220. Using configuration engine 220, a user of system 200 can specify the specific way these adverse events should be handled including how the adverse events should be processed by narrative generation engine 240 and which data structures in data sources 202, 204, and 206 can contain information associated with the adverse events. For example, configuration engine 220 can be configured to determine that a certain lab result values are of interest, perhaps based on regulatory, administrative, or other requirements, and should qualify as a specific event that is processed using a particular formatting or logic. Although the lab results can otherwise be interpreted as normal, configuration engine 220 can be instructed to identify specific criteria that cause those results to trigger an adverse event in the context of the clinical trials or study. In this way, configuration engine 220 can be used to customize system 200 to generate documents or narratives that specifically meet the needs of a study or data set Moreover, configuration engine 200 can provide an intuitive interface and language for selecting the criteria used for narrative generation. The interface can be provided, for example, using display device 218. Further examples of the user interface are provided in more detail below in reference to FIGS. 3-12. The input entered through the user interface via computing device 218 or via configuration script 216, can be entered using non-technical input and translated into a vector-oriented language for application to the prepared data sets. By doing this conversion, configuration engine can provide a user with easily understandable options and criteria without requiring complex technical knowledge from the user. Configuration engine 220, can map the human readable language used for input and configuration into the vector-oriented language used to process the datasets. By using a vector-oriented language or script, system 200 can efficiently apply the specified configuration to vectors of data set that contain the study information. In this way, a rule or condition specified by the user can be applied to all elements in the data set in an efficient manner to effectively determine what data should be used for the generated narrative.

Moreover, configuration engine 220 can allow for the user to create dynamic conjunctions or combinations of criteria or keywords. Configuration engine 220 can process this input into a computer readable instructions that can be applied to all of the elements of the available data sets. For example, a user can specify abnormal criteria that includes that the overall interpretation of the results is "abnormal" or that the overall interpretation of the results is "undetermined." Configuration engine 220 can map "overall interpretation" to a specific keyword containing that value in the data set and specify that if the value for the keyword is "undetermined" or "abnormal" for a given element of data, than that data should be included in the narrative. Additional examples of criteria that can be entered are demonstrated in relation to FIGS. 3 and 12, described in more detail below. Configuration engine 220, can map the input criteria to a vector-oriented language that is applied to the data sets. Vector-oriented languages, or array programming, can refer to a programming language optimized to generalize scalar operations to apply to vectors, matrices, or other high level or specialized data structures. Moreover, the vector-oriented language can utilize aliases to abstract the language from the data and can allow the script to be portable and applied to varied data sets in varied domains. The configuration generated by configuration engine 220 can be provided to data extraction engine 230 and narrative generation engine 240.

Moreover, configuration engine 220 can specify formatting or similar characteristics to use in the generated document or narrative. Using the above example, configuration engine 220 can specify that information related to the overall interpretation should be bolded for a value of "undetermined" and should be bold red text for a value of "abnormal." In this way, a user can use computing device 218 or configuration script 216 to instruct configuration engine 220 how to format the specified criteria. Configuration engine 220 can provide those formatting directives, along with the other instructions, to narrative generation engine 240 for use in generating the resulting narrative or document.

Data extraction engine 230 is a module that can utilize configuration information from configuration engine 220 and can retrieve a subset of data from the provided data sets for additional processing. For example, configuration engine 220 can specify a particular group of patients in a clinical study or a certain criteria that identifies a specific group of patients. Data extraction engine 230 can, using that list of patients or criteria, extract all relevant data records from the data sets that correspond to the determined group of patients. By extracting such data, data extraction engine 230 can reduce the overall size of the data set and ensure that only the data that will be relevant to the current patient is processed. Extracting relevant data is important because, in some embodiments, a document or narrative associated with every patient in a study is not necessary. Accordingly, the ability to extract data related to only those patients for whom a narrative is being generated reduces the computational overhead necessary to generate the narratives. This is particularly important, as each patient being processed may require multiple narratives or documents to be generated. Accordingly, reducing the amount of information that must be processed prior to analysis can greatly increase the computational efficiency of system 200. After extracting the relevant data records from the data set, data extraction engine 230 can provide the data records to narrative generation engine 240.

Narrative generation engine 240 is a module that can process multiple data elements using criteria and input from configuration engine 220 in order to generate a document or narrative 242 associated with the data. Narrative generation engine 240 gather the data for a patient specified by data extraction engine 220, and apply the vector-oriented instructions provided by configuration engine 220 to each record in the data set. Because configuration engine 220 already defines relevant criteria, narrative generation engine 240 can determine what data records, if any, in the relevant data set include values matching the defined criteria. In the example described above, narrative generation engine 240 can apply the vector-oriented instructions from configuration engine 220 to determine all records for a particular patient that show an "overall interpretation" of "undetermined" or "abnormal."

After determining data that matches the relevant criteria specified through configuration engine 220, narrative generation engine can use pre-existing document or narrative templates or narratives (e.g., narrative templates stored in data storage 215) for the relevant domain. Narrative generation engine 240 can populate the template using the data in the various data records for a particular patient. Additionally, narrative generation engine can use its determination of the data records matching the previously specified relevant criteria to populate portions of the clinical narrative associated with that data. For example, narrative generation engine 240 can generate a narrative that includes separate paragraphs or other notations indicating that the overall interpretation is either "undetermined" or "abnormal." Moreover, narrative generation engine 240 can utilize any formatting information provided by configuration engine 220 to properly format the relevant data. For example, the generated document can include in-text tables, summary text, charts, and graphs.

The narrative can be provided to a user on, for example, computing device 244. Additionally, the narratives can be stored in data storage 215 for later review or use. In some embodiments, narrative generation engine 240 can utilize previously generated narratives for the same patient. When generating a new narrative for that particular patient, narrative generation engine can make use of new data that has been gathered since the previous report was generated. Narrative generation engine 240 can compare the newly generated report with the previously generated report and provide differences that show what information changed between the two narratives. In some embodiments, differences can be shown using highlighting. In some embodiments, differences can be shown with comments or other annotations. For example, deleted items can be shown with strikethrough text. Moreover, if the previously generated report has been updated or annotated by a user, those annotations can be incorporated and displayed as part of the newly generated narrative.

FIGS. 3-12 are exemplary user interfaces for interacting with system 200. It is appreciated that these various user interfaces are exemplary, and are not intended to be an exhaustive list or diagram of the available user interface elements for interacting with and configuring system 200. Accordingly, many additional user interfaces, layouts, and control mechanisms are consistent with the disclosed embodiments.

Figure 3:
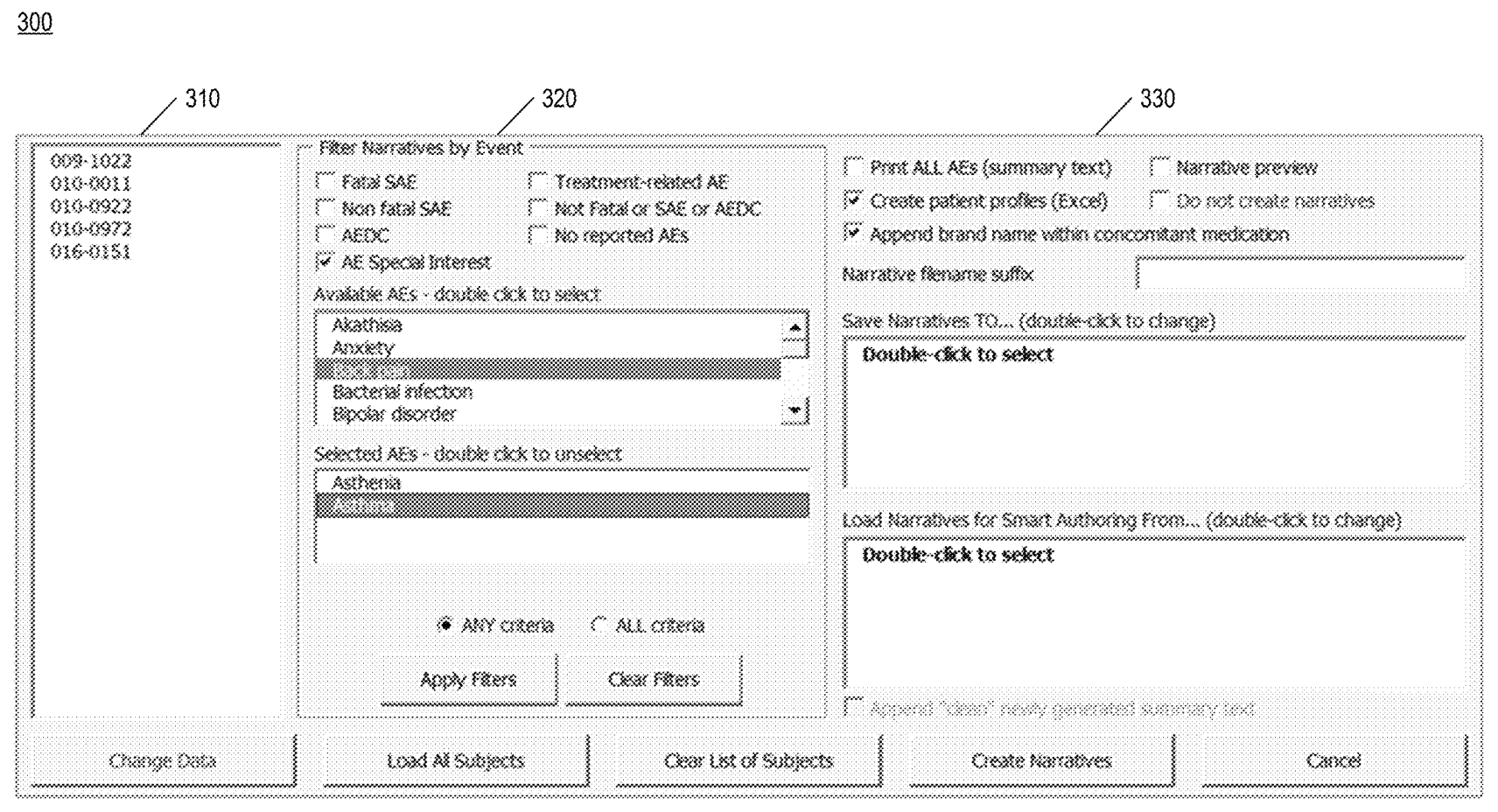

FIG. 3 is an exemplary user interface 300 for system 200 consistent with embodiments of the present disclosure. User interface 300 can be provided on, for example, computing device 218 or computing device 244. User interface 300 can provide a list of patient identifiers 310 for which a document or narrative will be generated by system 200. System 200 can receive the list of patient identifiers 310 through, for example configuration engine 220. In some embodiments, user interface 300 can represent an application executing natively on a computing device such as computing device 218 or computing device 244. In some embodiments, user interface 300 can represent a user interface executing natively but connecting to a data storage executing in a remote computing environment (e.g., a cloud storage or Electronic Document Management System).

User interface 300 can further include filters 320. Filters 320 can provide a mechanism further tailoring documents and narratives generated by system 200. As shown in FIG. 3, filters 320 can include checkboxes to select categories of adverse events that should be included in the narrative generation. Moreover, filters 320 can provide list boxes showing all available adverse events and selected adverse events. Using the controls in filters 320, a user using user interface 300 can select which adverse events are of interest, which can filter the set of patients for which narratives can be generated.

User interface 300 can also include narrative options 330. Narrative options 330 can provide controls to allow for additional configuration of the narrative output. For example, controls under narrative options 330 can allow the user to specify where narratives should be save (e.g., in storage 215), what narratives should be loaded for comparison with newly generated narratives (e.g., the existing narratives can be stored in storage 215), as well as other options for specifying narrative output on, for example, computing device 218 or computing device 244.

Figure 4A:
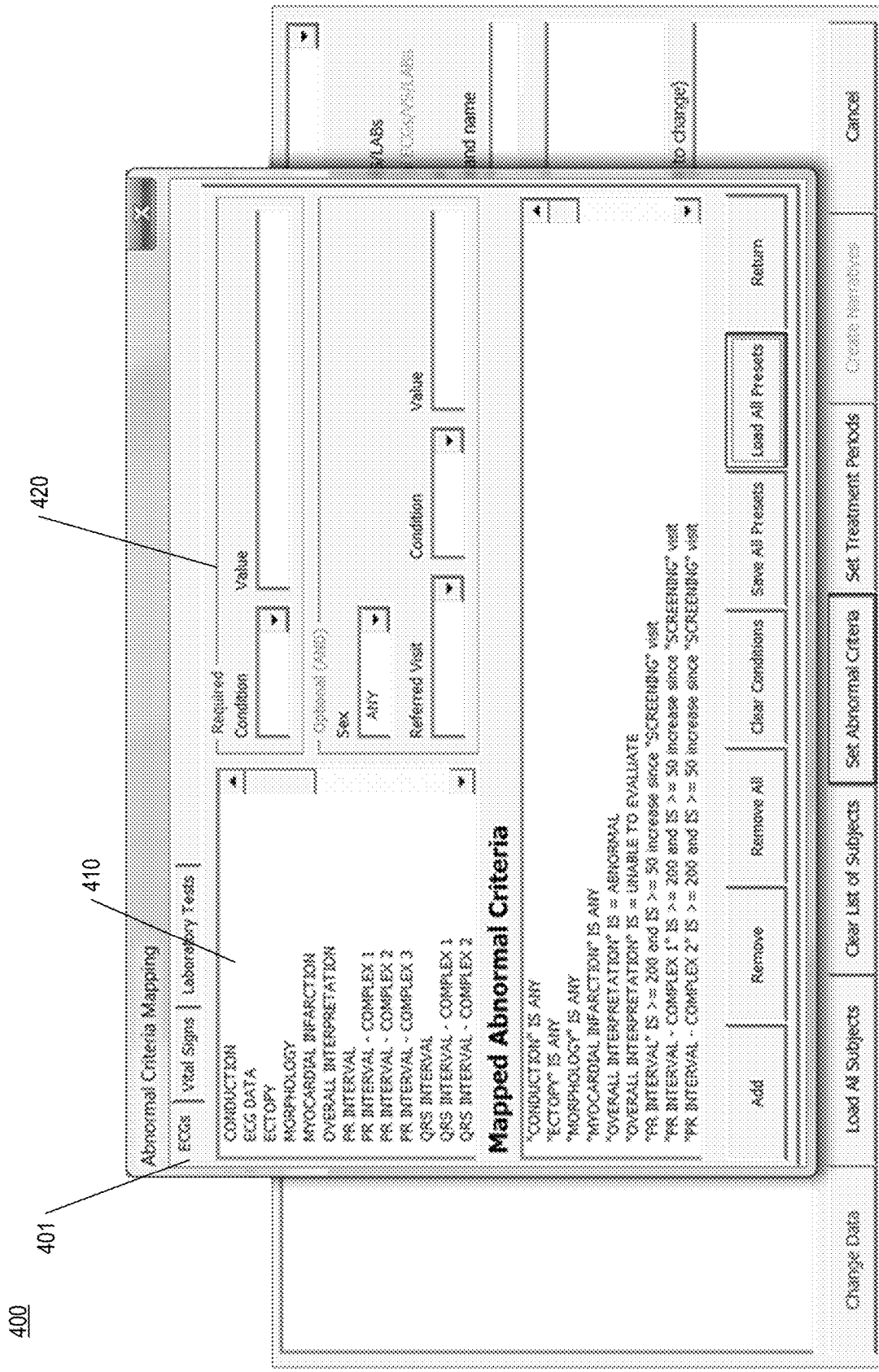
FIGS. 4A-4C are diagrams of exemplary user interfaces, consistent with embodiments of the present disclosure.
Figure 4B:
Figure 4C:

FIGS. 4A-4C are exemplary embodiments of a user interface dialog box 400 for use with a user interface (e.g., user interface 300 of FIG. 3), consistent with embodiments of the present disclosure. User interface dialog box 400 and the various depicted embodiments are exemplary and are not intended to be an exhaustive representation of the options and dialogs provided to configure or interact with system 200. User interface dialog box 400 can be provided on, for example, computing device 218 or computing device 244.

FIG. 4A is an exemplary tab 401 of user interface dialog box 400 for system 200 consistent with embodiments of the present disclosure. Tab 401 can be used to select abnormal criteria for generation of documents or narratives. The abnormal criteria can be used by configuration engine 220 and applied to clinical data by narrative generation engine 240. Tab 401 can include condition list 410. As shown, condition list 410 can include specific conditions or categories associated with a particular treatment or test or a test name itself (e.g., an electrocardiogram ("ECG")). A user can select a specific condition, keyword or category from condition list 410 and can use the controls provided in abnormal condition options 420 to choose values and tests to apply to the data. By choosing condition criteria using condition list 410 and condition options 420, a user can configure system 200 (e.g., through configuration engine 220) to find data that matches the specified condition variables. Matching data can then be included or emphasized in the generated narratives (e.g., by narrative generation engine 240).

FIG. 4B is an exemplary tab 402 of user interface dialog box 400 for system 200 consistent with embodiments of the present disclosure. Tab 402 can, similar to tab 401 in FIG. 4A, be used to select abnormal criteria for generation of documents or narratives. The abnormal criteria can be used by configuration engine 220 and applied to clinical data by narrative generation engine 240. Similar to tab 401 of FIG. 4A, tab 402 can include condition list 413 and condition options 420. Condition list 413, however, can provide different categories of conditions than condition list 410 of FIG. 4A. As shown in FIG. 4B, condition list 413 can be associated with vital signs of a patient. As described above in relation to FIG. 4A, a user can use tab 402 to configure criteria for narrative generation using condition list 413 and condition options 420.

FIG. 4C is an exemplary tab 403 of user interface dialog box 400 for system 200 consistent with embodiments of the present disclosure. Tab 403 can, similar to tab 401 in FIG. 4A and tab 402 in FIG. 4B, be used to select abnormal criteria for generation of documents or narratives. The abnormal criteria can be used by configuration engine 220 and applied to clinical data by narrative generation engine 240. Similar to tab 401 and tab 402 described above, tab 403 can include condition list 416 and condition options 420. Condition list 416 can provide different categories of conditions than condition list 410 of tab 401 and condition list 413 or tab 402. As shown in FIG. 4C, condition list 416 can be associated with laboratory test results. As described above in relation to FIGS. 4A and 4B, a user can use tab 403 to configure criteria for narrative generation using condition list 416 and condition options 420.

Figure 5:
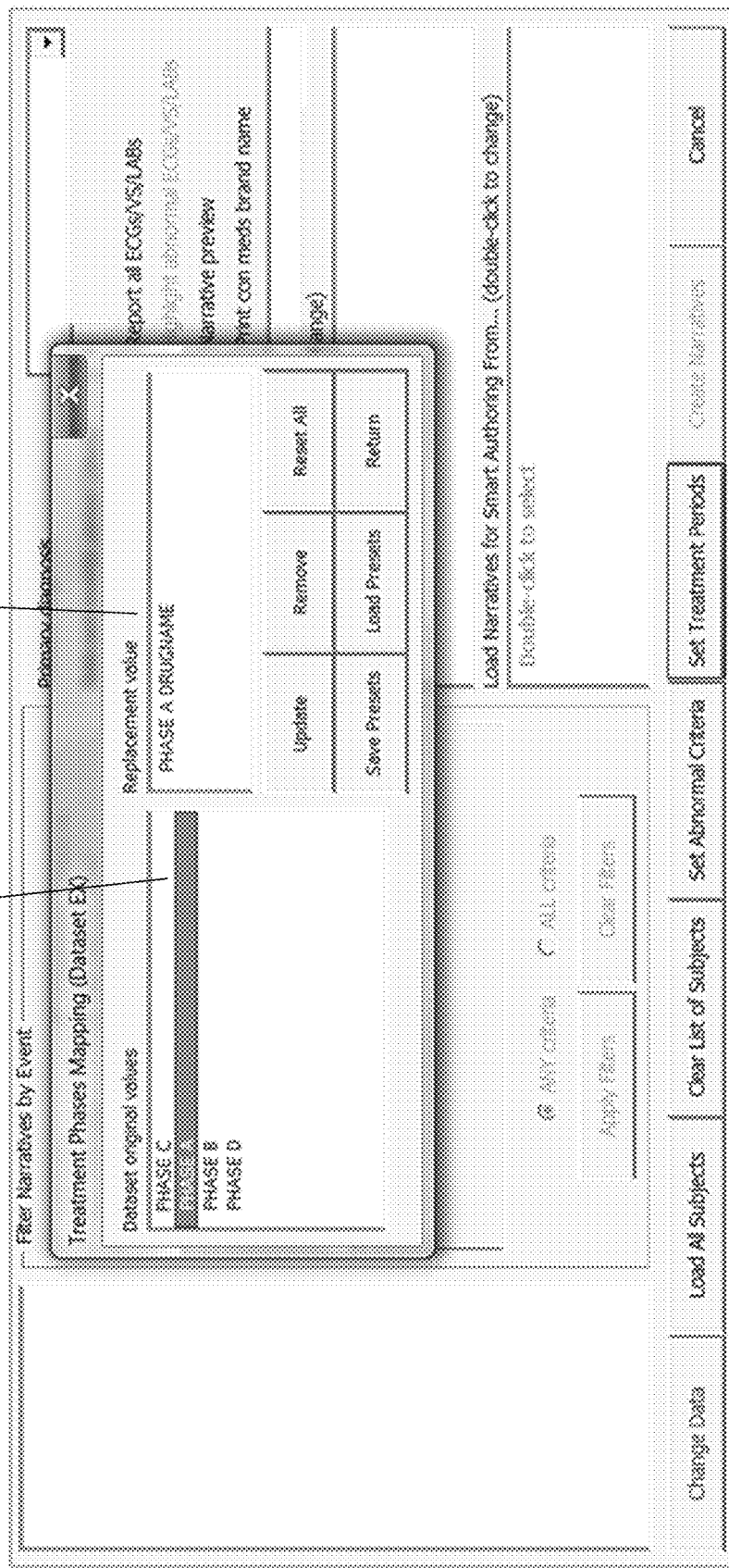
FIG. 5 is a diagram of an exemplary user interface, consistent with embodiments of the present disclosure.

FIG. 5 is an exemplary embodiments of a user interface dialog box 500 for use with a user interface (e.g., user interface 300 of FIG. 3), consistent with embodiments of the present disclosure. User interface dialog box 500 is exemplary and is not intended to be an exhaustive representation of the options and dialogs provided to configure or interact with system 200. User interface dialog box 500 can be provided on, for example, computing device 218 or computing device 244. User interface dialog box 500 can allow a user to map particular values or keywords associated with the data set being processed with names to be used in the document or narrative creation. For example, as shown in FIG. 5, user interface dialog box 500 can include dataset original values 510 showing keywords or values found in the data set being processed. User interface dialog box 500 can include replacement value box 520. In some embodiments, when a value or keyword is selected in dataset original values 510, the corresponding replacement value used in the narrative can be shown in replacement value box 520. Moreover, user interface dialog box 500 can be used to update, modify, delete, create, load or save one or more replacement values for a selected value or multiple values in dataset original values 510.

FIGS. 6-12 are exemplary user interfaces (e.g., user interfaces 600, 700, 800, 900, 1000, 1100, and 1200) for interacting with system 200 consistent with embodiments of the present disclosure. These user interfaces can be provided on, for example, computing device 218 or computing device 244. In some embodiments, user interfaces 600-1200 can be part of a web service or web application executing on a web server and displayed through a desktop or mobile web browser (e.g., MOZILLA FIREFOX, APPLE SAFARI, MICROSOFT INTERNET EXPLORER, MICROSOFT EDGE, GOOGLE CHROME, or similar). Computing device 218 or computing device 244 can provide system 200, a web server with access to system 200, and the web browser connecting to the web server and providing user interfaces 600-1200, or some combination thereof. In some embodiments, system 200 can execute on computing devices separate from the computing devices providing the web server and/or web browser that provides user interfaces 600-1200. In these embodiments, the web server and/or web browser can connect remotely to the computing device executing system 200.

Figure 6A:
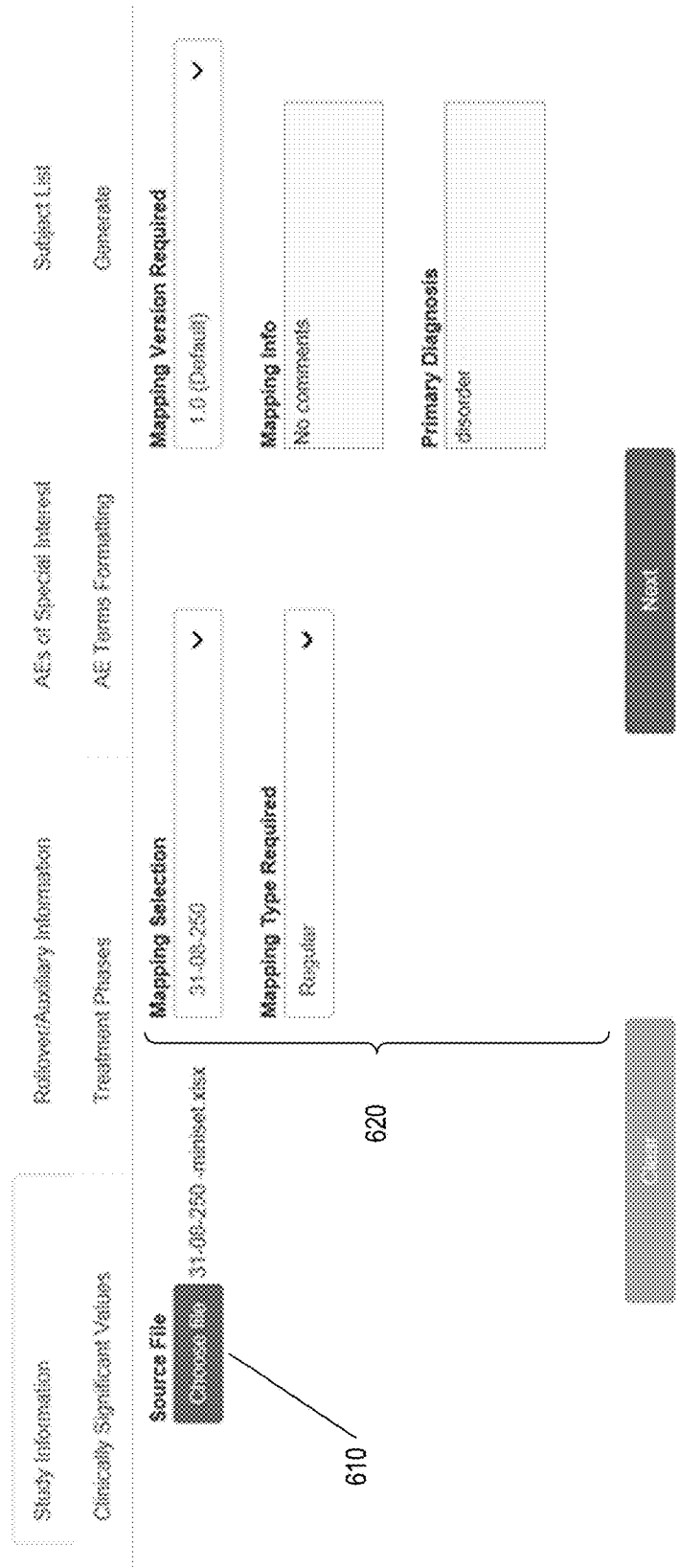
FIG. 6A is a diagram of an exemplary user interface, consistent with embodiments of the present disclosure.

FIG. 6A is an exemplary user interface 600 for system 200 consistent with embodiments of the present disclosure. User interface 600 can provide source file selector 610 that can be used to select a source dataset for document or narrative generation. Additionally, user interface 600 can provide study information options 620 that can allow a user to provide general parameters or information about the study and/or documents or narratives that will be generated.

Figure 6B:
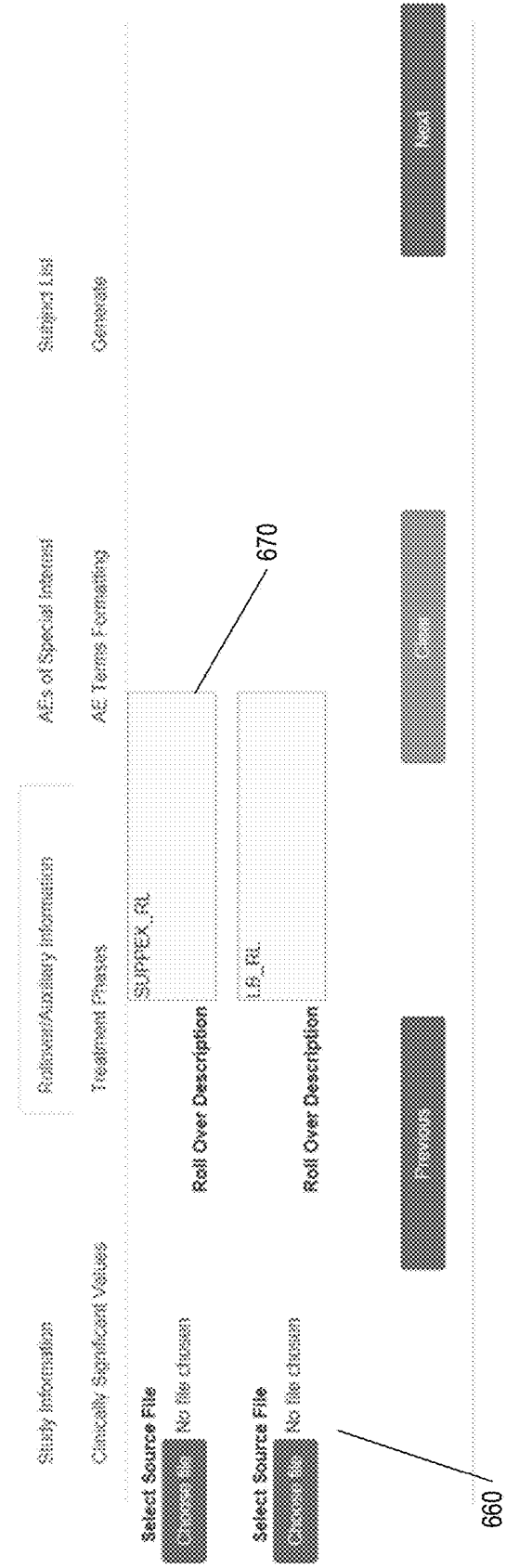
FIG. 6B is a diagram of an exemplary user interface, consistent with embodiments of the present disclosure.

FIG. 6B is an exemplary user interface 650 for system 200 consistent with embodiments of the present disclosure. User interface 600 can provide additional source file selector 660 that can be used to select a source dataset for rollover data. Rollover data can be data related to patients who participated in a previous study. User interface 650 can include multiple source file selectors 660 for selecting multiple source files with rollover data. Additionally, user interface 650 can provide rollover description box 670 that can be used to describe the rollover data when it is included in the current set of data. Using user interface 650, system 200 can utilize additional source files for rollover data. Additionally, user interface 650 can support raw data which was provided as a physically separate file(s) from source file selector 610.

Figure 7:
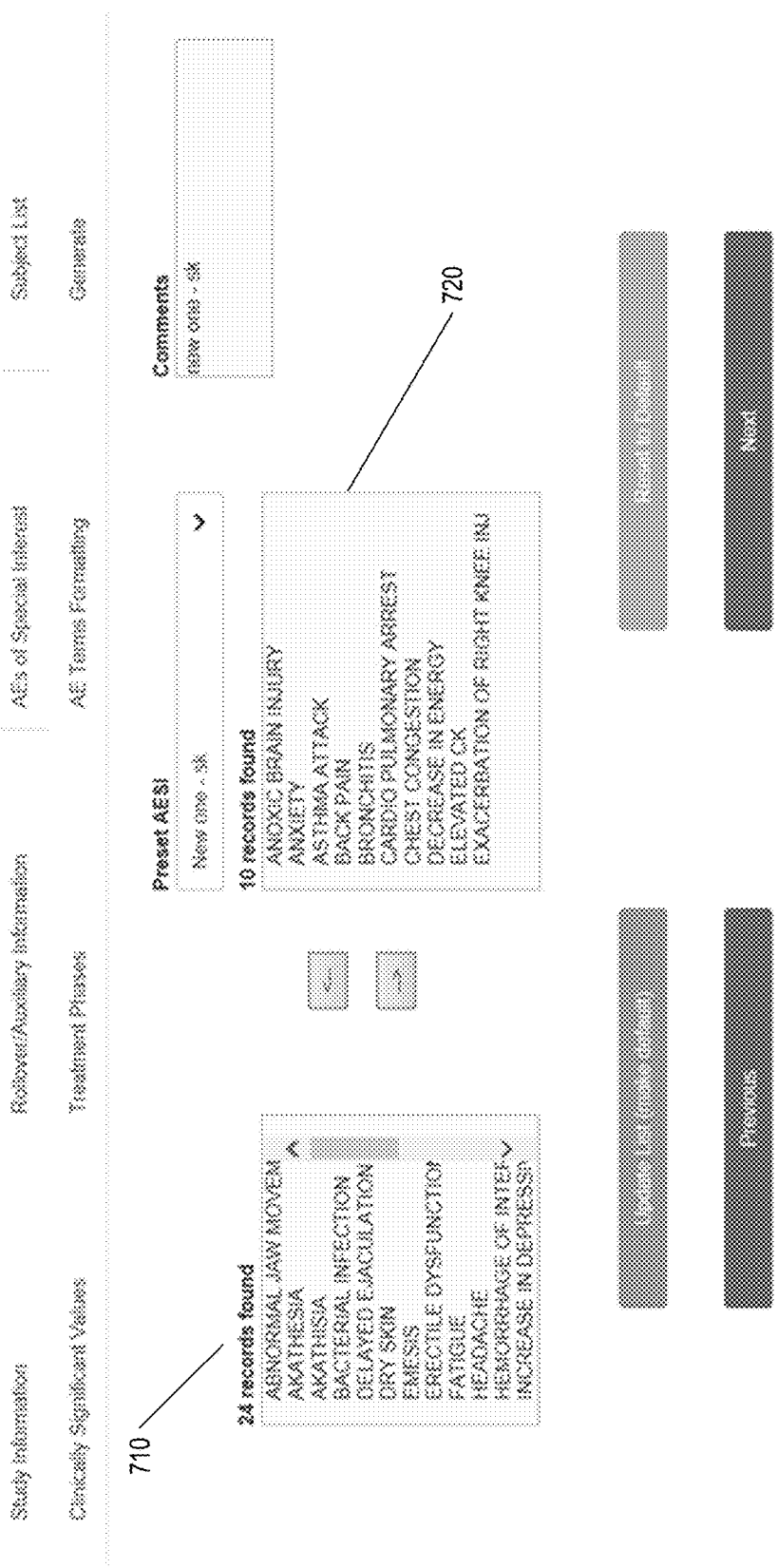
FIG. 7 is a diagram of an exemplary user interface, consistent with embodiments of the present disclosure.

FIG. 7 is an exemplary user interface 700 for system 200 consistent with embodiments of the present disclosure. User interface 700 can provide adverse events that can be selected to trigger the document or narrative generation. User interface 700 can provide adverse event records 720 that categorized as adverse events of special interest. Additionally, user interface 700 can provide adverse event records 710 that show additional adverse event records that have been found but are not selected to trigger the document or narrative generation. Using user interface 700, a user can moved selections from one list to the other to control which adverse events are included in the generated documents or narratives.

Figure 8:
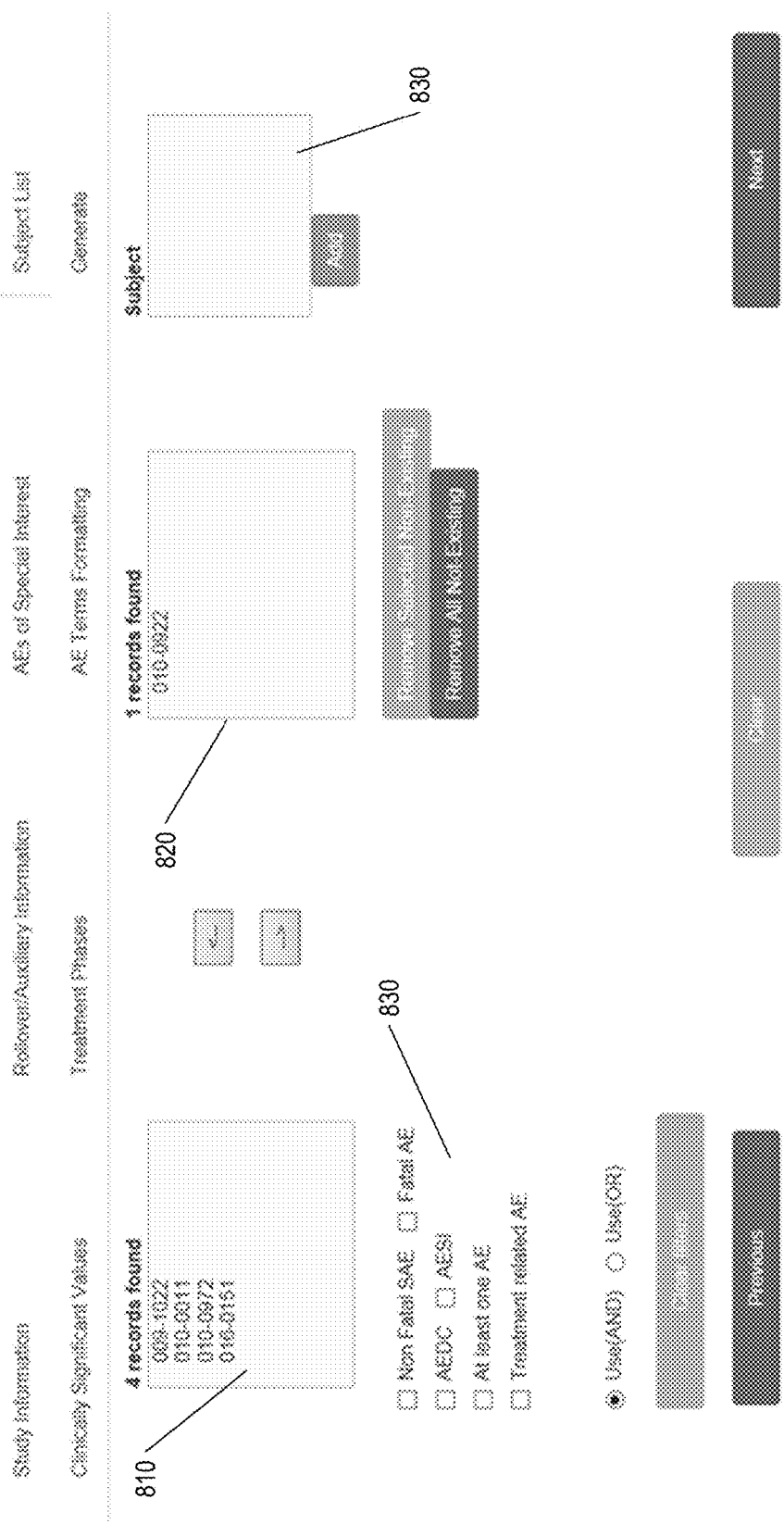
FIG. 8 is a diagram of an exemplary user interface, consistent with embodiments of the present disclosure.

FIG. 8 is an exemplary user interface 800 for system 200 consistent with embodiments of the present disclosure. User interface 800 can provide patient or individual identifiers that are in the data set being processed. Similar to user interface 700 described above, user interface 800 can provide selected patient identifiers 820 and can provide unselected patient identifiers 810 in the dataset. Using user interface 800, a user can moved selections from one list to the other to control which patient data is processed for the generated documents or narratives. User interface 800 can further provide filters 830 that can be used to dynamically filter selected individuals based on the types of adverse events associated with the individuals represented in the dataset. After selecting an adverse event or combination of adverse events from filters 830, individuals not matching the selected criteria can be excluded from the document or narrative generation. Additionally, user interface 800 can provide subject input 830 which can be used to add additional subjects or patient identifiers. Using subject input 830, a user can specify additional patients for which narratives should be generated.

FIG. 9 is an exemplary user interface 900 for system 200 consistent with embodiments of the present disclosure. User interface 900 can provide an interface for selecting conditions, criteria, or pre-populated flags provided within the data for inclusion in the generated documents or narratives. User interface 900 can provide selection box 910 for selecting specific types of medical tests or categories. As shown in FIG. 9, selection box 910 can allow for the selection of "Clinical Laboratory Tests," "ECG Results," and "Vital Signs." The count, order, and/or naming shown in selection box 910 can be dynamically controlled within configuration engine 220. Each of these medical test names can include multiple tests or keywords that can be displayed in tests list 920. It is appreciated that the three categories listed are only exemplary, and that other categories or test names may be available in the data set being processed and presented through medical test names 910. After selecting a medical test name from medical test names 910, a user can select specific tests from tests list 920, and specific criteria and conditions 930. Using the elements of user interface 900, a user can specify a plurality of criteria that can be used during the processing of the datasets. The rules or criteria created can be provided to system 200 (e.g., through configuration engine 220) to determine the information that is included in the generated documents or narratives.

Figure 10:
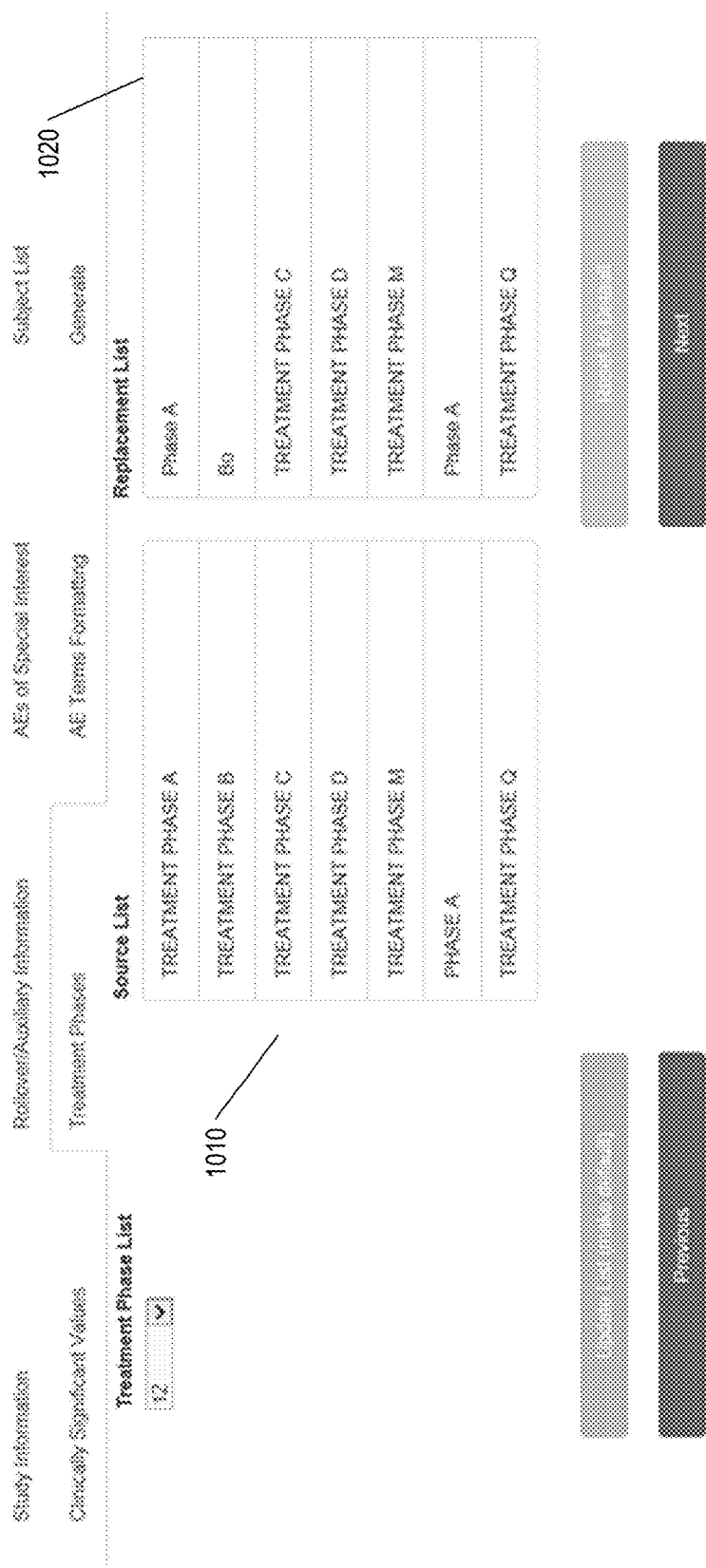
FIG. 10 is a diagram of an exemplary user interface, consistent with embodiments of the present disclosure.

FIG. 10 is an exemplary user interface 1000 for system 200 consistent with embodiments of the present disclosure. User interface 1000 can provide an interface for substituting text labels for treatment phases of clinical trials. User interface 1000 can provide source list 1010. Source list 1010 can represent the clinical phases in the dataset. Replacement list 1020 can represent the names or labels of the clinical phases to be used in the generation of documents or narratives. Through user interface 1000, system 200 can be directed to rename treatment phases appearing in the source data in order to provide consistent output in the generated documents or narratives.

Figure 11:
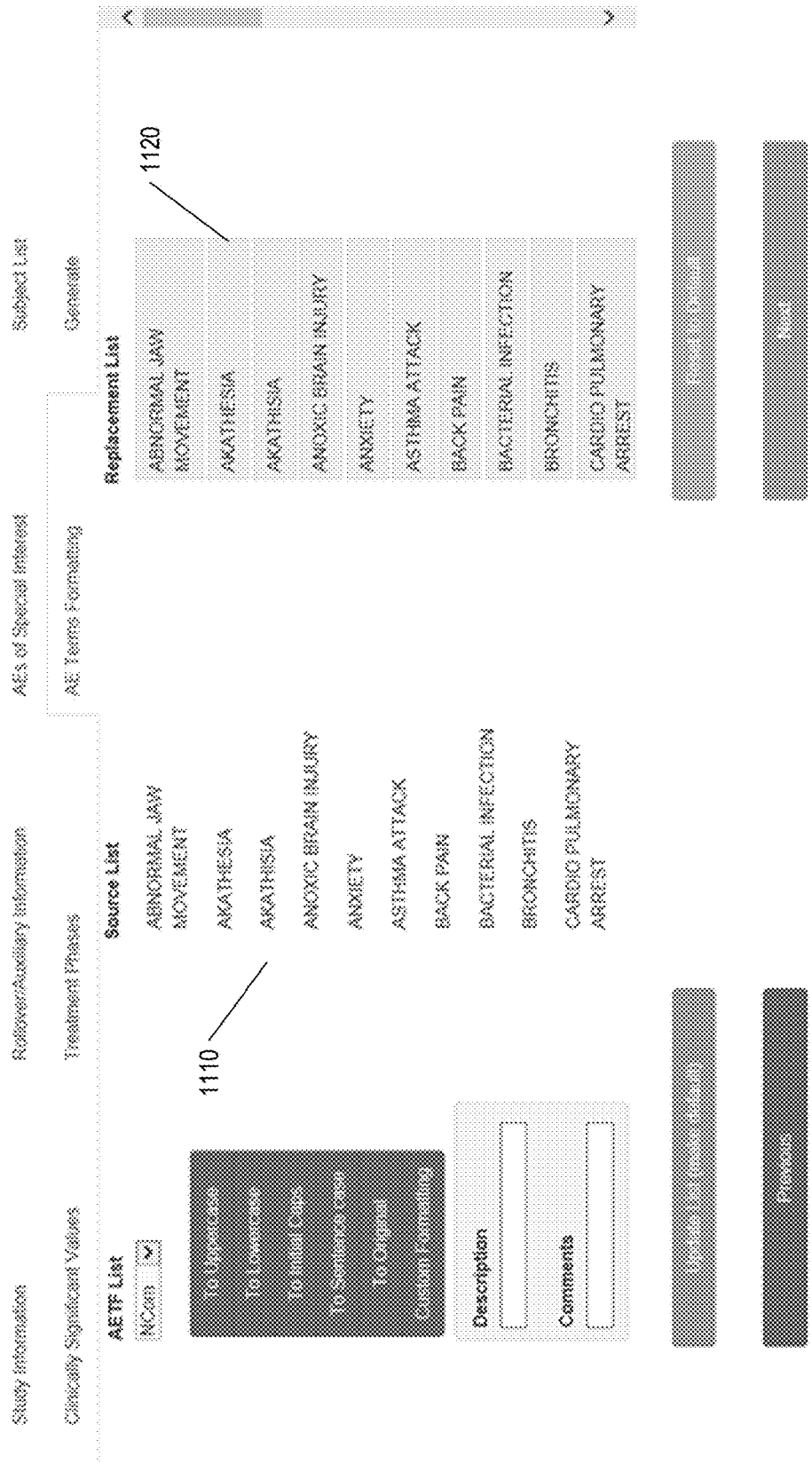
FIG. 11 is a diagram of an exemplary user interface, consistent with embodiments of the present disclosure.

FIG. 11 is an exemplary user interface 1100 for system 200 consistent with embodiments of the present disclosure. User interface 1100 can provide an interface for mapping the labels of adverse events used in the document or narrative creation. User interface 1100 can provide source list 1110. Source list 1110 can represent the adverse event names found in the dataset. Replacement list 1120 can represent the names or labels of the adverse events to be used in the generation of documents or narratives. Through user interface 1100, system 200 can be directed to rename adverse events appearing in the source data in order to provide consistent output in the generated documents or narratives.

Figure 12:
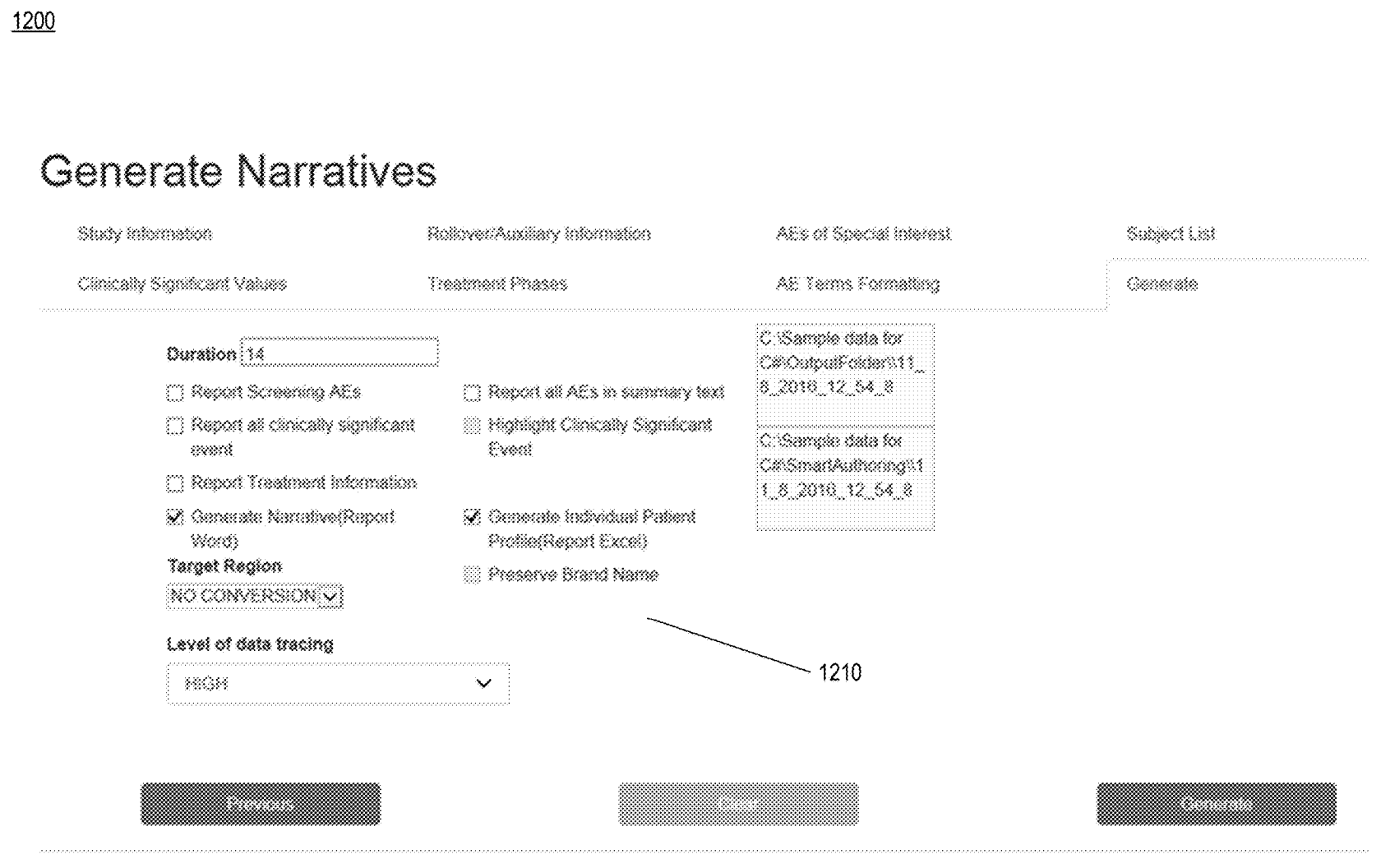

FIG. 12 is an exemplary user interface 1200 for system 200 consistent with embodiments of the present disclosure. User interface 1200 can provide an interface for configuring options for the document or narrative creation. User interface 1200 can provide output options 1210. These output options can be used to control the level of detail and type of events that are reported in the generated documents or narratives.

Figure 13:
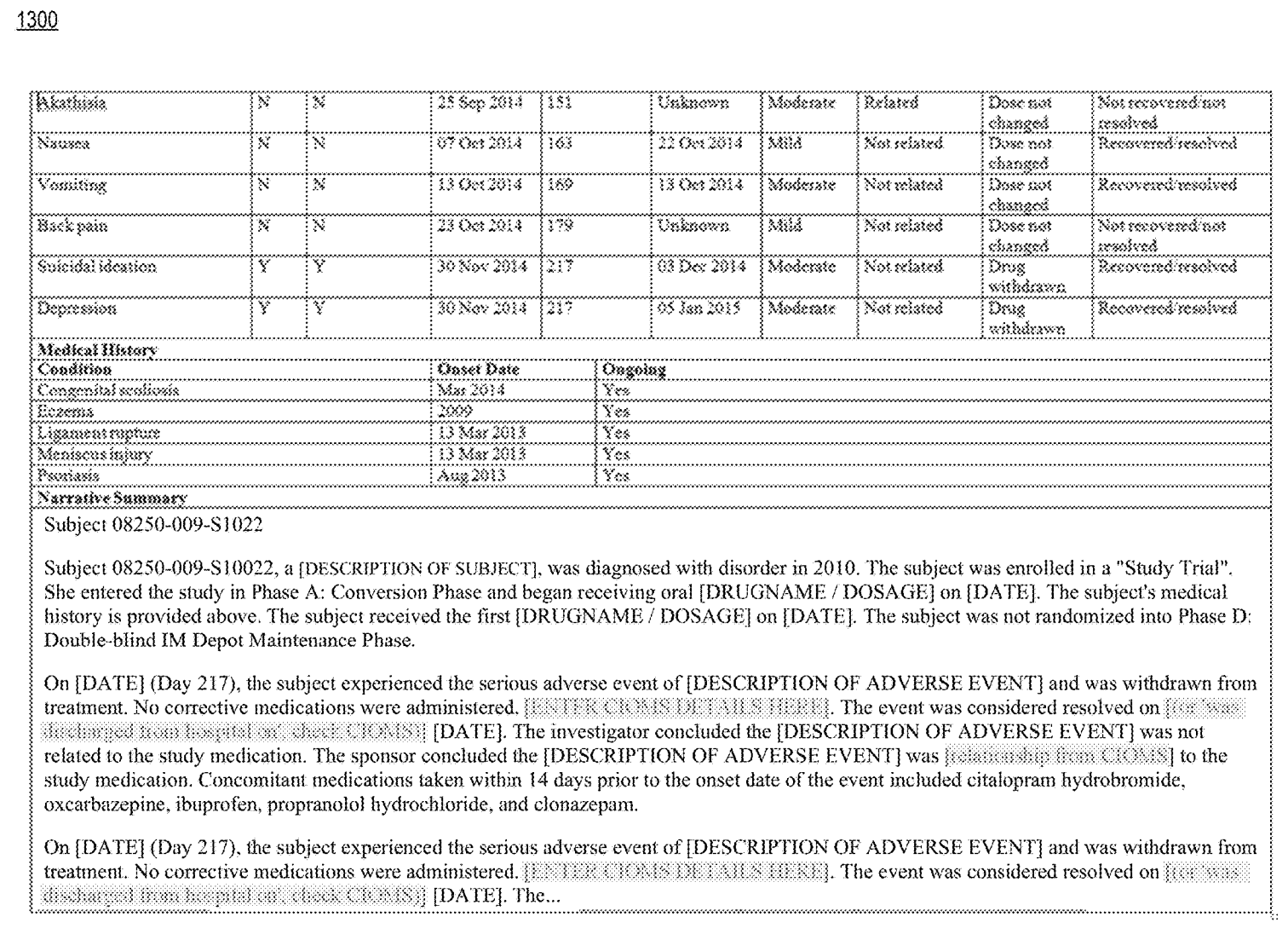

FIG. 13 is an exemplary narrative 1300 consistent with embodiments of the present disclosure. Narrative 1300 can represent a narrative generated by system 200. As shown in FIG. 13, narrative 1300 can include tabular data representing the adverse events experienced by a particular individual. Additionally, narrative 1300 can include medical history showing past conditions, the onset date, and if the conditions are still ongoing. Moreover, using data from the datasets, system 200 can include textual descriptions of the relevant clinical study and adverse events experienced by the individual. As shown in FIG. 13, narrative 1300 can include placeholders where additional information can be entered by those running the study. Narrative 1300 can be based on a template that includes specified areas of text that are generated by system 200 (e.g., by narrative generation engine 240).

Figure 14:
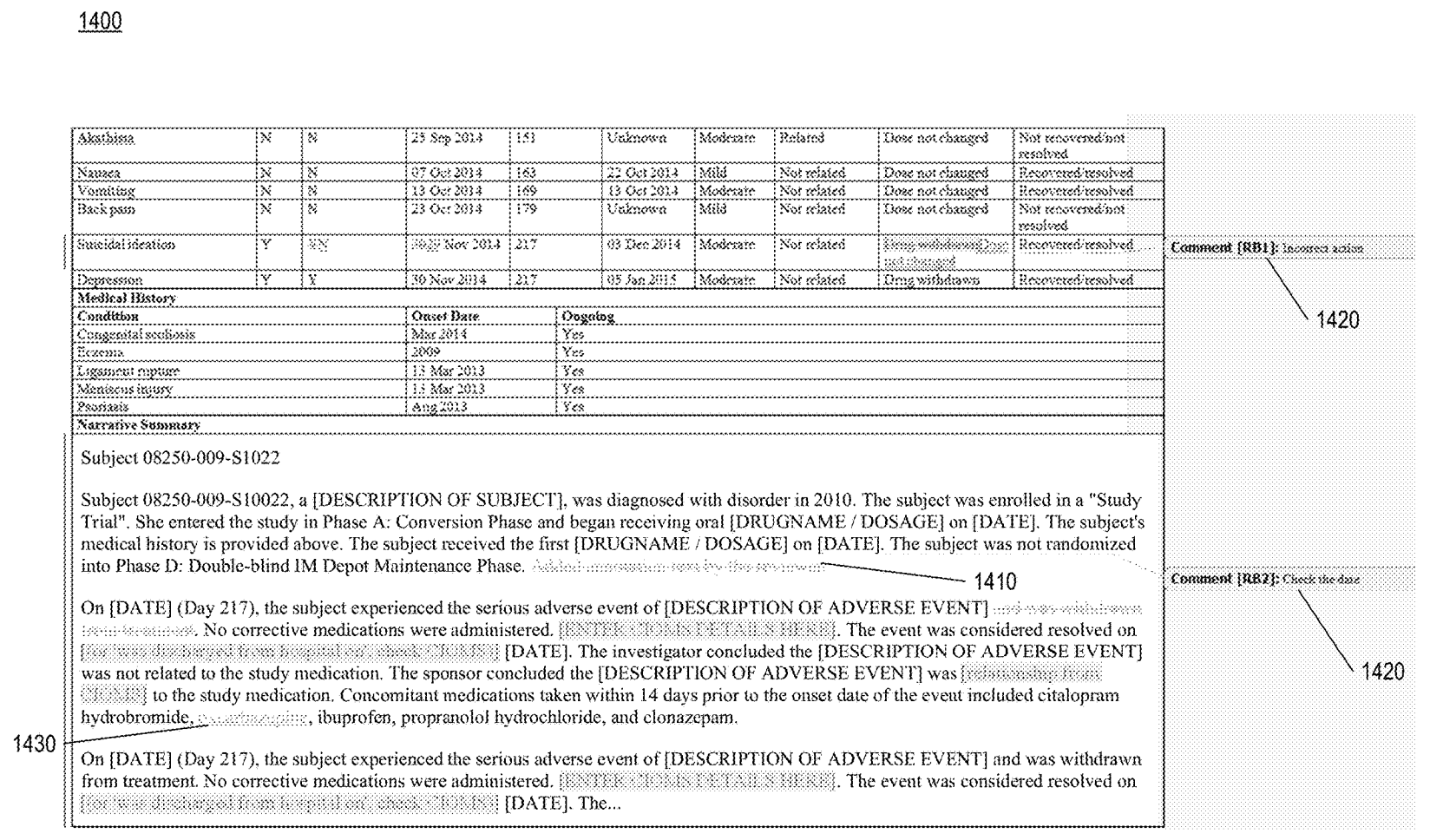

FIG. 14 is an exemplary narrative 1400 consistent with embodiments of the present disclosure. Narrative 1400 can represent an updated narrative generated by system 200 (e.g., through narrative generation engine 240). Narrative 1400 can be an updated version of the narrative represented in FIG. 13. Narrative 1400 can display differences between the previously generated narrative (e.g., narrative 1300 in FIG. 13) and the current narrative. For example, narrative 1400 can show data that has been updated using strikethrough text 1410 for the previous data and underlined text for the new data. Additionally, comments 1420 or other custom annotations added manually can be retained in the updated narrative 1400. Moreover, new data can be represented with underlined text 1430 and inserted into narrative 1400 where appropriate. Using these annotations, system 200 can generate updated narratives 1400 that clearly indicate portions of narrative 1400 that have changed based on newly available data.

Figure 15:
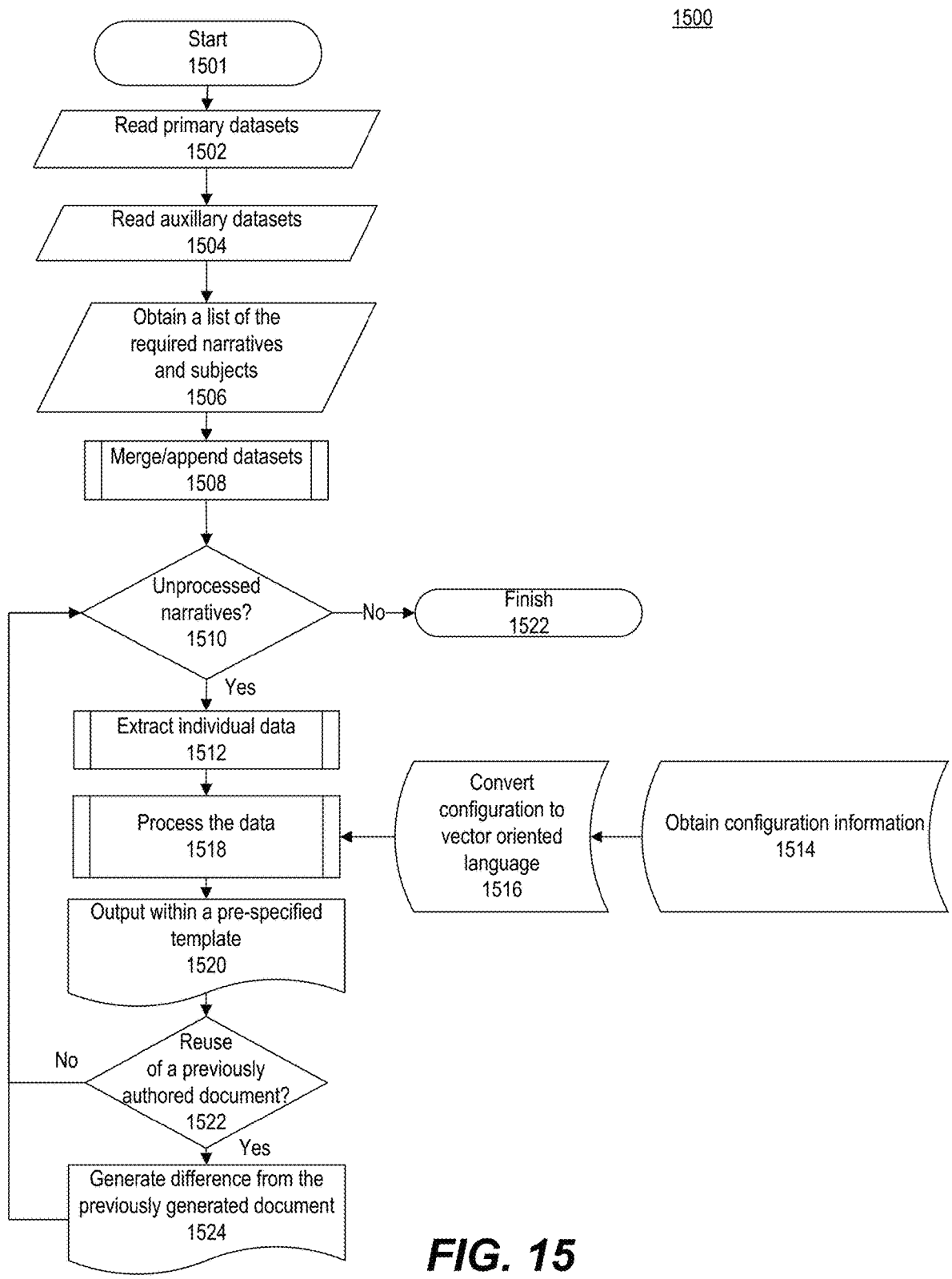
FIG. 15 is a flowchart of an exemplary method for data driven document creation and modification, consistent with embodiments of the present disclosure.

FIG. 15 is flowchart of an exemplary method 1500 for data driven document creation and modification. After initial step 1501, the system (e.g., system 200 of FIG. 2) can read (step 1502) primary datasets (e.g., using data intake engine 210 of FIG. 2). The primary datasets can include clinical trial information associated with patients or individuals taking part in a particular study or set of clinical trials. The system can further read (step 1504) auxiliary data sets (e.g., using data intake engine 210). Auxiliary data sets can include additional information about a clinical study or participants in a clinical study. The Auxiliary data sets can include past clinical trials associated with individuals in the current study. In some embodiments, auxiliary data sets can include demographic information or other ancillary data associated with the current study.

The system can further obtain (step 1506) a list of required narratives and subjects (e.g., using configuration engine 220 of FIG. 2, user interface 300 of FIG. 2, or user interface 800 of FIG. 8). The list of subjects can include all subjects participating in a study or a subset of the subjects participating in a study. Moreover, the list of subjects can be further filtered based on the types of adverse events experienced by the participants in the study.

The system can merge or append (step 1508) datasets that contain information relevant to the narratives and documents being generated. The system can utilize the various data sources and create a unified data set that can be processed be the system. Data sets having different formats or structures can be normalized into a consistent format for further processing.

If no narratives need to be processed (step 1510) then method 1500 can end (step 1522.) Otherwise, the system can extract (step 1512) individual data from the unified data set that is associated with the particular subject or narrative currently being generated. The data relevant data can be retrieved from the unified data set.

The system can obtain (step 1514) configuration information from users (e.g., using user interfaces 300-1200 of FIGS. 3-12). As described above the configuration information can include the types of adverse events to include specific criteria to be matched in the data sets, and specific values that may represent important attributes for the study. The configuration information can be provided, for example, through configuration engine 220. The system can further convert (step 1516) the configuration provided to the system into a vector oriented language or instructions (e.g., using configuration engine 220) that can be efficiently applied to the datasets being processed. The system can process (step 1518) the datasets using the generated vector oriented language or instructions. The intermediate results from processing the datasets can be presented using, for example, device 244. After processing the datasets based on the specific configuration information provided, the system can output (step 1520) information associated with a particular subject or narrative using a pre-specified template. The output narrative (e.g., narrative 1300 of FIG. 13) can represent the dataset in a consistent format for use in analyzing the study. The system can determine (step 1522) if a previously authored document or narrative is being reused. If not, the system can return to step 1510 and determine if additional narratives are needed. If a previously authored document is being reused, the system can generate (step 1524) a difference file (e.g., narrative 1400) that shows the various changes between the original narrative (e.g., narrative 1300) and the new data. The system can then return to step 1510 to determine if additional narratives need processed.

In the foregoing specification, embodiments have been described with reference to numerous specific details that can vary from implementation to implementation. Certain adaptations and modifications of the described embodiments can be made. For example, some embodiments consistent with the present disclosure include support for rollover patients that participated in previous studies. Other embodiments can be apparent to those skilled in the art from consideration of the specification and practice of the invention disclosed herein. It is intended that the specification and examples be considered as exemplary only. It is also intended that the sequence of steps shown in figures are only for illustrative purposes and are not intended to be limited to any particular sequence of steps. As such, those skilled in the art can appreciate that these steps can be performed in a different order while implementing the same method.

What is claimed is:

1. A method for updating a document comprising:
    obtaining, by one or more computing devices, data that indicates criteria including one or more limiting conditions that identify a portion of a data set, the one or more limiting conditions including entity identifying criteria, the entity identifying criteria defining a cross-section of a population that have experienced a same adverse event;
    generating, by one or more computing devices and using a vector-oriented language, a data filter that includes one or more filtering parameters configured to be applied to a superset of entities, wherein the one or more filtering parameters a re determined using the obtained data;
    filtering, by one or more computing devices, the superset of entities using the generated data filter to identify a filtered subset of entities that satisfy the entity identifying criteria;
    for each particular entity in the filtered subset of entities:
        accessing, by one or more computing devices, data records associated with the particular entity;
        detecting, by one or more computing devices, each data record of the accessed data records that is indicative of an abnormal entity state;
        selecting, by one or more computing devices, a pre-existing template based on a domain of the accessed data records;
        populating, by one or more computing devices, the selected template using at least some of the data in the detected data records indicative of an abnormal entity state;
        determining, by one or more computing devices, that the document for the particular entity already exist in a database, wherein the document includes a first narrative describing prior data from prior data records associated with the particular entity;
        generating a second narrative data from each detected data record indicative of an abnormal entity state, wherein the first and second narrative data are in prose form;
        updating, by one or more computing devices, based on the first narrative, the existing document in the database to include (i) the populated template and (ii) the second narrative, wherein updating the existing document comprises identifying one or more differences between the first narrative and the second narrative by comparing the first narrative and the second narrative; and causing, by one or more computing devices, the updated document to be displayed showing the differences between the first narrative and the second narrative.

2. The method of claim 1, wherein:
the cross-section of the population includes each entity that participated in a particular clinical study; and
the entity identifying criteria include data that indicates one or more demographic characteristics associated with the entity.

3. The method of claim 1, wherein updating the existing document further comprises:
annotating, by one or more computing devices, the updated portions of the document, wherein the differences between the first narrative and the second narrative comprise the annotations.

4. The method of claim 1, wherein generating the data filter comprises:
translating, by one or more computing devices, the obtained data into one or more abstract filtering parameters that are data source independent.

5. The method of claim 1, wherein:
the first narrative comprises first text;
the second narrative comprises second text; and
the differences between the first narrative and the second narrative comprise one or more modifications to the first text to obtain the second text.

6. The method of claim 5, wherein the one or more modifications comprise:
at least one of (i) one or more words or phrases added to the first text or (ii) one or more or phrases removed from the first text, wherein:
the one or more words or phrases that are added are displayed in a first format; or
the one or more words or phrases that are removed are displayed in a second format.

7. The method of claim 1, further comprising:
providing, by one or more computers, to a display device, an interface and language for narrative generation;
receiving an input via the interface, the input comprising human readable language;
translating the human readable language into the vector-oriented language for application to the data sets wherein a rule or condition is applied to all elements in the data sets to determine which data to use for generation of at least one of the first narrative or the second narrative, wherein the vector-oriented language comprises a program language to generalize scalar operations to apply to vectors and abstract language from the data.

8. The method of claim 1, wherein:
the first narrative comprises one or more placeholders, wherein additional information is entered to at least some of the one or more placeholders configured to have additional information entered; and
the second narrative comprises at least some of the data from the detected data records entered into at least one of the one or more placeholders.

9. The method of claim 1, wherein detecting each data record of the accessed data records that is indicative of the abnormal entity state comprises:
determining one or more data records of the accessed data records that includes data matching at least one specified condition, wherein the at least one specified condition indicates criteria for classifying a result represented by the data as being abnormal.

10. A system for generating a document, the system comprising:
one or more computing devices including a processor and programmed with instructions to:
obtain, by the one or more computing devices, data that indicates criteria including one or more limiting conditions that identify a portion of a data set, the one or more limiting conditions including entity identifying criteria, the entity identifying criteria defining a cross-section of a population that have experienced a same adverse event;
generate, bythe one or more computing devices and using a vector-oriented language, a data filter that includes one or more filtering parameters configured to be applied to a superset of entities, wherein the one or more filtering parameters are determined using the obtained data;
filter, by the one or more computing devices, the superset of entities using the generated data filter to identify a filtered subset of entities that satisfy the entity identifying criteria;
for each particular entity in the filtered subset of entities: access, by the one or more computing devices, data records associated with the particular entity;
detect, by the one or more computing devices, each data record of the accessed data records that is indicative of an abnormal entity state;
select, by the one or more computing devices, a pre-existing template based on a domain of the accessed data records;
populate, by the one or more computing devices, the selected template using at least some of the data in the detected records indicative of an abnormal entity state;
determine, by the one or more computing devices, that the document for the particular entity already exist in a database, wherein the document includes a first narrative describing prior data from prior data records associated with the particular entity;
generate a second narrative data from each detected data record indicative of an abnormal entity state, wherein the first and second narrative data are in prose form;
update, by the one or more computing devices, based on the first narrative, the existing document in the database to include (i) the populated template and (ii) the second narrative, wherein updating the existing document comprises identifying one or more differences between the first narrative and the second narrative by comparing the first narrative and the second narrative; and
cause, by one or more computing devices, the updated document to be displayed showing the differences between the first narrative and the second narrative.

11. The system of claim 10, wherein:
the cross-section of the population includes each entity that participated in a particular clinical study; and
the entity identifying criteria include data that indicates one or more demographic characteristics associated with the entity.

12. The system of claim 10, wherein the existing document being updated comprises the one or more computing devices being programmed to:
annotate, by the one or more computing devices, the updated portions of the document, wherein the differences between the first narrative and the second narrative comprise the annotations.

13. The system of claim 10, wherein the data filter being generated comprises the one or more computing devices being programmed to:
translate, by the one or more computing devices, the obtained data into one or more abstract filtering parameters that are data source independent.

14. One or more non-transitory computer-readable storage media storing instructions that, when executed by one or more computing devices, cause the one or computing devices to:
obtain data that indicates criteria including one or more limiting conditions that identify a portion of a data set, the one or more limiting conditions including entity identifying criteria, the entity identifying criteria defining a cross-section of a population that have experienced a same adverse event;
generate, using a vector-oriented language, a data filter that includes one or more filtering parameters configured to be applied to a superset of entities, wherein the one or more filtering parameters are determined using the obtained data;
filter the superset of entities using the generated data filter to identify a filtered subset of entities that satisfy the entity identifying criteria; for each particular entity in the filtered subset of entities:
access data records associated with the particular entity;
detect each data record of the accessed data records that is indicative of an abnormal entity state;
select a pre-existing template based on a domain of the accessed data records;
populate the selected template using at least some of the data in the detected data records indicative of an abnormal entity state;
determine that a document for the particular entity already exist in a database, wherein the document includes a first narrative describing prior data from prior data records associated with the particular entity;
generate a second narrative data from each detected data record indicative of an abnormal entity state, wherein the first and second narrative data are in prose form;
update, based on the first narrative, the existing document in the database to include (i) the populated template and (ii) the second narrative, wherein updating the existing document comprises identifying one or more differences between the first narrative and the second narrative by comparing the first narrative and the second narrative; and
cause the updated document to be displayed showing the differences between the first narrative and the second narrative.

15. The one or more non-transitory computer-readable storage media of claim 14, wherein:
the cross-section of the population includes each entity that participated in a particular clinical study; and
the entity identifying criteria include data that indicates one or more demographic characteristics associated with the entity.

16. The one or more non-transitory computer-readable storage media of claim 14, wherein the existing document being updated comprises the one or more computing devices being programmed to:
annotate the updated portions of the document, wherein the differences between the first narrative and the second narrative comprise the annotations.

17. The one or more non-transitory computer-readable storage media of claim 14, wherein the data filter entities being generated comprises the one or more computing devices being programmed to:
translate the obtained data into one or more abstract filtering parameters that are data source independent.

* * * * *